United States Patent
Shelley et al.

(10) Patent No.: US 11,004,541 B1
(45) Date of Patent: May 11, 2021

(54) SYSTEMS AND METHODS FOR DETERMINING A GENOMIC TESTING STATUS

(71) Applicant: Flatiron Health, Inc., New York, NY (US)

(72) Inventors: Addison Shelley, New York, NY (US); Alexander Padmos, New York, NY (US); Angel Leung, Richmond, VA (US); Chun-Che Wang, Seattle, WA (US); Dominic Green, Yorktown Heights, NY (US); Edward Liu, Brooklyn, NY (US); Janet Donegan, Park City, UT (US); Lauren Sutton, Cary, NC (US); Lucy He, New York, NY (US); Sharang Phadke, Plainsboro, NJ (US)

(73) Assignee: FLATIRON HEALTH, INC., New York, NY (US)

( * ) Notice: Subject to any disclaimer, the term of this patent is extended or adjusted under 35 U.S.C. 154(b) by 0 days.

(21) Appl. No.: 17/076,502

(22) Filed: Oct. 21, 2020

Related U.S. Application Data

(60) Provisional application No. 62/923,684, filed on Oct. 21, 2019.

(51) Int. Cl.
*G16B 40/00* (2019.01)
*G16H 10/60* (2018.01)
*G16B 45/00* (2019.01)
*G16B 50/00* (2019.01)

(52) U.S. Cl.
CPC ............. *G16B 40/00* (2019.02); *G16B 45/00* (2019.02); *G16B 50/00* (2019.02); *G16H 10/60* (2018.01)

(58) Field of Classification Search
CPC ........ G16B 40/00; G16B 45/00; G16B 50/00; G16H 10/60
USPC .......................................................... 702/19
See application file for complete search history.

(56) References Cited

U.S. PATENT DOCUMENTS

| | | | |
|---|---|---|---|
| 2006/0184475 A1 | 8/2006 | Krishnan et al. | |
| 2016/0103973 A1 | 4/2016 | Singal et al. | |
| 2018/0068083 A1 | 3/2018 | Cohen et al. | |
| 2019/0287681 A1* | 9/2019 | Sathe | G06N 20/20 |

OTHER PUBLICATIONS

International Search Report and Written Opinion in international Application No. PCT/US2020/056699, dated Feb. 4, 2021 (16 pgs.).

* cited by examiner

*Primary Examiner* — Jerry Lin
(74) *Attorney, Agent, or Firm* — Finnegan, Henderson, Farabow, Garrett & Dunner, LLP

(57) ABSTRACT

A computer-implemented system for determining a genomic testing status of a patient may include at least one processor programmed receive, from a source, unstructured information from a plurality of patient records associated with a patient; determine, using a first machine learning model, a primary patient record from among the plurality of patient records, wherein at least a portion of information represented in the primary patient record correlates to genomic testing; determine, using a second machine learning model and based on unstructured information from one at least one of the patient records, a likelihood of an occurrence of genomic testing for the patient; determine a genomic testing status of the patient based on the determined likelihood of the occurrence of genomic testing; and display a user interface comprising an indicator of the genomic testing status of the patient and a link to the primary patient record.

21 Claims, 16 Drawing Sheets

400A

Biomarkers

Structured biomarker in EMR ⓘ

EGFR — Positive
Lab: 2/14/2019

Wildtype
staging: 11/15/2016

ALK — Negative
Staging: 11/15/2016

Inferred genomic testing status from EMR ⓘ
Patient has had genomic testing — Likely
View document — 02/19/2019
⊗ Confirm patient has had genomic testing — Tested   Not tested

Research team captured biomarker(s) ⓘ
⊕ Provide biomarker status for patient matching

Drug order history

Carboplatin — First Order: 01/02/2029
Last Order: 02/10/2019

Biomarkers

Structured biomarker in EMR ⓘ

EGFR                                          Positive
                                       Lab: 2/14/2019

Wildtype
                                    staging: 11/15/2016

ALK                                          Negative
                                    Staging: 11/15/2016

Inferred genomic testing status from EMR ⓘ

Patient has had genomic testing    Verified by user as tested
View document                                 last update by
Edit genomic testing status ✏          janedoe@flatiron.com
                                                06/15/2018

Research team captured biomarker(s) ⓘ

⊕ Provide biomarker status for patient matching

Drug order history

Carboplatin                          First Order: 01/02/2029
                                      Last Order: 02/10/2019

Biomarkers

402

Structured biomarker in EMR ⓘ

EGFR — Positive
Lab: 2/14/2019

Wildtype
staging: 11/15/2016

ALK — Negative
Staging: 11/15/2016

404

Inferred genomic testing status from EMR ⓘ

Patient has had genomic testing — Verified by user as tested
View document — last update by
Edit genomic testing status ✏ — janedoe@flatiron.com
06/15/2018

406

Research team captured biomarker(s) ⓘ

ⓧ Patient is confirmed to have been tested for this biomarker:

[ *Select biomarker ⇵ ] [ *Enter result date 📅 ]
[ *Provide test result ⇵ ] [ Additional description ]
[ Select test vendor ⇵ ] [ Select test type ⇵ ]

— 406B

Add to patient profile — 406C

408

Drug order history

Carboplatin — First Order: 01/02/2029
Last Order: 02/10/2019

Biomarkers

Structured biomarker in EMR ⓘ

EGFR                                    Positive
                                   Lab: 2/14/2019

Wildtype
                               staging: 11/15/2016

ALK                                     Negative
                               Staging: 11/15/2016

Inferred genomic testing status from EMR ⓘ
Patient has had genomic testing    Verified by user as tested
View document                              last update by
Edit genomic testing status ✎       janedoe@flatiron.com
                                              06/15/2018

Research team captured biomarker(s) ⓘ
Last update by janedoe@flatiron.com on 02/25/2019

EGFR ✎                                 Wildtype
Comprehensive Genomic Profiling (CGP)  Result date: 02/24/2019

⊕ Provide biomarker status for patient matching ——— 406A

Drug order history

Carboplatin                    First Order: 01/02/2029
                                Last Order: 02/10/2019

Biomarkers

Structured biomarker in EMR ⓘ

EGFR
Positive
Lab: 2/14/2019

Wildtype
staging: 11/15/2016

ALK
Negative
Staging: 11/15/2016

Inferred genomic testing status from EMR ⓘ

Patient has had genomic testing    Verified by user as tested
View document    last update by
Edit genomic testing status ✏    janedoe@flatiron.com
    06/15/2018

Research team captured biomarker (1) ⓘ
Last update by janedoe@flatiron.com on 02/25/2019
EGFR ✏    Wildtype
Comprehensive Genomic Profiling (CGP)    Result date: 02/24/2019

─────────────────────────────────────

ⓧ Patient is confirmed to have been tested for this biomarker:

| *Select biomarker ⬍ | 02/24/2019 📅 |
| *Provide test result ⬍ | Additional description |
| * Provide test entity ⬍ | Select test type ⬍ |

Add to patient profile

Drug order history

Carboplatin
First Order: 01/02/2029
Last Order: 02/10/2019

Biomarkers

Structured biomarker in EMR ⓘ

EGFR  Positive
  Lab: 2/14/2019

Wildtype
  staging: 11/15/2016

ALK  Negative
  Staging: 11/15/2016

Inferred genomic testing status from EMR ⓘ
Patient has had genomic testing  Verified by user as tested
View document  last update by
Edit genomic testing status ✏  janedoe@flatiron.com
  06/15/2018

Research team captured biomarker(s) ⓘ
Last update by janedoe@flatiron.com on 02/25/2019

EGFR ✏  Wildtype
Comprehensive Genomic Profiling (CGP)  Result date: 02/24/2019

PD-L1 ✏  High (>=50%)
Immunohistochemistry (IHC)  Dako 22c3
  result delivered: 02/24/2019

⊕ Provide biomarker status for patient matching

Drug order history

Carboplatin  First Order: 01/02/2029
  Last Order: 02/10/2019

Feasibility analysis

Demographic and visit criteria

Genders: [Any genders]
Locations: [Any locations]

☐ Exclude deceased patients   ☐ Include new patients only ⓘ

Visits between
[📅] and [📅]

Age
[Age minimum] [Age maximum]

---

Diagnostic criteria

Diagnoses: [Any disease]

Genomic testing statuses ⓘ: [Any testing statuses]

Stages: [Any stages]

Metastatic statuses ⓘ: [Any metastatic statuses]

Biomarkers ⓘ
☑ Include research team captured biomarker(s)

[Any of] [BRAF] [Selected result]

---

Treatment related criteria

Inclusionary drugs: [All of] [Any drugs]

Medication orders after: [📅]

Exclusionary drugs: [None of] [Any drugs]

Medication orders after: [📅]

Apply

≡ | Trials  Patients  Feasibility  Reports | Q Search  ⊙ Jane Doe

602 — Feasibility analysis
604 — Demographic and visit criteria
Genders
[ Any genders ▼ ]            ☐ Exclude deceased patients  ☐ Include new patients only ⓘ
Locations                    Visits between
[ Any locations ▼ ]          [ 📅 ]  and  [ 📅 ]
Age
[ Age minimum ] [ Age maximum ]

606 — Diagnostic criteria
Diagnoses
[ Non-small cell lung cancer ▼ ]
Genomic testing statuses ⓘ
[ Tested only ▼ ]            Stages
Biomarkers ⓘ                 [ Any stages ▼ ]
☑ Include research team captured biomarker(s)
                             Metastatic statuses ⓘ
[ Any of ▼ ]  [ Selected result ▼ ]   [ Metastatic only ▼ ]
[ BRAF ▼ ]
⊕ Add another biomarker criteria 608 — Treatment related criteria
Inclusionary drugs           Exclusionary drugs
[ All of ▼ ]                 [ None of ▼ ]
[ Any drugs ▼ ]              [ Any drugs ▼ ]
Medication orders after      Medication orders after
[ 📅 ]                       [ 📅 ]
                    [ Apply ]

612 — Patients matching criteria (3)
                        ⌒614                                  Showing all of 3 patients  >>|
☐ | Patient       | Diagnosis              |                | Primary physician | Location    | Current status on trial(s)
☐ | Research team captured data |          |                |                   |             |
☐ | Jane Johnson  | Non-small cell lung    | ML inference   | Smith, Carol      | East clinic | BRE-0015  ● Active

Trials  Patients  Feasibility  Reports

Patients matching criteria (3)

| Research team captured data | ML inference | | | |
|---|---|---|---|---|

Showing all of 3 patients >>|

| Patient | Diagnosis | Primary physician | Location | Current status on trial(s) |
|---|---|---|---|---|
| ☐ Jane Johnson | Non-small cell lung | Smith, Carol | East clinic | BRE-0015 ● Active |
| ☐ Genelle Larson | Breast Cancer | Klocko, Dagmar | South Aletha | ORM-2321 ⊘ Pending |
| ☐ Christina Weissnat | Breast Cancer | Barrows, Aurelia | Cancer Specialists | ORM-2321 ● Inactive |

614a → Jane Johnson row
614b → Genelle Larson row
614c → Christina Weissnat row 614 (callout to ML inference box)

🔍 Search  ● Jane Doe

*FIG. 6C*

SYSTEMS AND METHODS FOR DETERMINING A GENOMIC TESTING STATUS

CROSS-REFERENCE TO RELATED APPLICATION

This application claims the benefit of priority of U.S. Provisional Patent Application No. 62/923,684, filed Oct. 21, 2019, the contents of which are incorporated herein by reference in their entirety.

BACKGROUND

Technical Field

The present disclosure relates to systems and methods for determining a genomic testing status of a patient.

Background Information

The cancer research community is constantly faced with a challenge of identifying patients who are eligible for clinical trials. There are often many barriers that may prevent a patient from participating in a clinical trial. For example, identifying a patient at just the right time such as, for instance, when they are ready to be put on a therapy but have not yet started one, is challenging when a practice may have dozens of trials open, each with a dozen or more inclusion and/or exclusion criteria, and with hundreds of patients coming into a practice per day (or even greater numbers across practices). Further complicating the process is the fact that a genomic testing status of a patient may change suddenly from one day to the next, and this change may only be captured in a handwritten note by a physician. This can lead to patients who do have a disqualifying genomic testing status being placed in trials for which they do not qualify, disrupting the results of the trial. Moreover, this can lead to patients who have a qualifying genomic testing status to be excluded from trials they may otherwise qualify for. Thus, to overcome these challenges, it is desirable to identify eligible patients for a clinical trial and eligible trials for a patient more efficiently based on a genomic testing status. Additionally, it is desirable to predict a likelihood of genomic testing for a patient (e.g., whether or not genomic testing has occurred at least once for a patient), to accurately and efficiently coordinate the matching of patients to trials.

SUMMARY

Embodiments consistent with the present disclosure include systems and methods for determining a genomic testing status of a patient. Embodiments of the present disclosure may overcome one or more aspects of existing techniques for determining trials based on computer-generated algorithms involving genomic statuses. The use of computer-generated algorithms in accordance with embodiments of the present disclosure thus allows for faster and more efficient ways for providing patients, physicians, and researchers with reliable suggestions of eligible trials that may benefit the patients.

In an embodiment, a device for determining a genomic testing status of a patient may include at least one processor programmed to: receive, from a source, unstructured information from a plurality of patient records associated with a patient; determine, using a first machine learning model, a primary patient record from among the plurality of patient records, wherein at least a portion of information represented in the primary patient record correlates to genomic testing; determine, using a second machine learning model and based on unstructured information from one at least one of the patient records, a likelihood of an occurrence of genomic testing for the patient; determine a genomic testing status of the patient based on the determined likelihood of the occurrence of genomic testing; and display a user interface comprising an indicator of the genomic testing status of the patient and a link to the primary patient record.

In an embodiment, a method for determining trials using a genomic testing status of a patient may include receiving, from a source, a plurality of patient records associated with a patient; determining, using a first machine learning model, a primary patient record from among the plurality of patient records, wherein at least a portion of information represented in the primary patient record correlates to genomic testing; determining, using a second machine learning model and based on at least one of the patient records, a likelihood of an occurrence of genomic testing for the patient; determining a genomic testing status of the patient based on the determined likelihood of the occurrence of genomic testing; and displaying a user interface comprising an indicator of the genomic testing status of the patient and a link to the primary patient record.

In an embodiment, a non-transitory computer-readable medium may include instructions that when executed by one or more processors, cause the one or more processors to: receive, from a source, a plurality of patient records associated with a patient; determine, using a first machine learning model, a primary patient record from among the plurality of patient records, wherein at least a portion of information represented in the primary patient record correlates to genomic testing; determine, using a second machine learning model and based on at least one of the patient records, a likelihood of an occurrence of genomic testing for the patient; determine a genomic testing status of the patient based on the determined likelihood of the occurrence of genomic testing; and display a user interface comprising an indicator of genomic testing status of the patient and a link to the primary patient record.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIGS. 4A, 4B, 4C, 4D, 4E, and 4F are diagrams illustrating exemplary user interfaces for providing information of a patient and suggested trials, consistent with the present disclosure.

FIG. 5 is a diagram illustrating an exemplary user interface for surfacing patient records, consistent with the present disclosure.

FIGS. 6A, 6B, and 6C are diagrams illustrating exemplary user interfaces for providing feasibility analysis.

DETAILED DESCRIPTION

Figure 1:
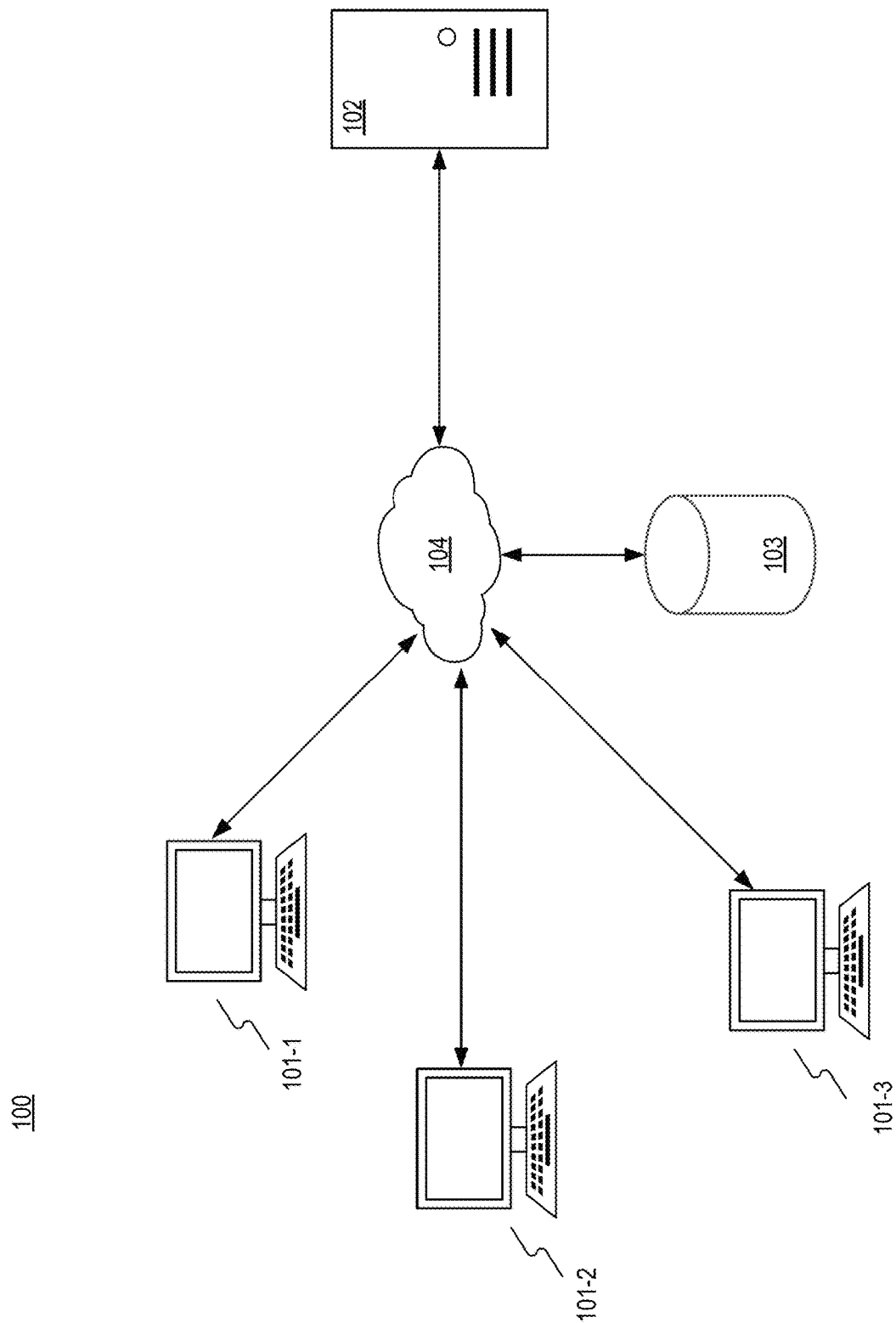
FIG. 1 is a block diagram illustrating an exemplary system for providing one or more suggested patients for a trial or one or more suggested trials for a patient, consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions, or modifications may be made to the components illustrated in the drawings, and the illustrative methods described herein may be modified by substituting, reordering, removing, repeating, or adding steps to the disclosed methods. Moreover, any of the steps in the illustrative methods may be performed consecutively or simultaneously. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, non-volatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

In this disclosure, a system for selecting one or more patients for a trial and/or selecting one or more trials for a patient, based on a genomic testing status, is disclosed.

FIG. 1 illustrates an exemplary system 100 for implementing embodiments consistent with the present disclosure, described in detail below. As shown in FIG. 1, system 100 may include one or more client devices 101, a computing device 102, a database 103, and a network 104. It will be appreciated from this disclosure that the number and arrangement of these components are exemplary and provided for purposes of illustration. Other arrangements and numbers of components may be used without departing from the teachings and embodiments of the present disclosure.

A client device 101 (e.g., client device 101-1, 101-2, 101-3) may be configured to receive user input from a user for creating a new trial and/or to perform any step of any process discussed herein. For example, client device 101 may reside at a clinic, and a user (e.g., a physician or administrator) may enter information for creating a new trial portfolio at an input device (such as an input device 153) of client device 101. A trial portfolio may include a group of trials, a group of trials meeting certain criteria, patient information for a group of patients for a trial, or any other information relating to creating or managing a trial. Client device 101 may include a processor, memory, input device, output device, or other computing component. For example, client device 101 may have components corresponding to those of computing device 102. By way of example, the user may enter an identification number (e.g., a National Clinical Trial (NCT) number or ClinicalTrials.gov identifier) at an interface of client device 101 for creating a new trial, and client device 101 may transmit the identification number to computing device 102. Computing device 102 may create a trial portfolio for the new trial based on the identification number. Client device 101 may also receive and present information received from computing device 102. For example, client device 101 may receive information relating to suggested patients for one or more trials from computing device 102 and present the information at an interface of client device 101 to the user. In some embodiments, client devices 101-1, 101-2, and 101-2 may reside at the same site or different sites.

Computing device 102 may be configured to receive information from client device 101 for creating the new trial portfolio from client device 101. Computing device 102 may also create a trial portfolio based on the information received from computing device 102. The trial information received by computing device 102 may include at least a portion of trial eligibility criteria associated with the trial, such as a genomic testing eligibility restriction. Computing device 102 may also create a new trial portfolio for the trial based on the trial information. The trial portfolio may include one or more trial eligibility criteria for determining whether a patient is eligible for the trial. For example, trial eligibility criteria may include a genomic testing restriction that an eligible patient must have a verified genomic testing status. Computing device 102 may further automatically generate an algorithm for suggesting one or more eligible patients for the new trial based on the trial eligibility criteria (sometimes referred to herein as an "patient-trial matching algorithm"). For example, computing device 102 may automatically generate an algorithm representing an expression tree based on the trial eligibility criteria, and the nodes and/or leaves of the expression tree may represent the trial eligibility criteria. In some embodiments, a strength of eligibility may be determined, which may be based on a degree to which a patient matches a set of criteria. For example, a patient matching 90% of a set of criteria may have a higher strength of eligibility than a patient matching 50% of a set of criteria. As another example, a patient with a verified genomic testing status including an indicator of "tested" may have a higher strength of eligibility for a trial having an eligibility restriction of "tested" than a patient who only has a predicted genomic testing status having an indicator of "tested" (or even another indicator) that has not been verified. In some embodiments, a strength of eligibility may be stored and/or transmitted by a client device 101, a computing device 102, and/or any other device suitable for managing patient data. In some embodiments, a strength of eligibility may be determined for criteria that are designated as preferred but not for criteria designated as absolute restrictions on eligibility (e.g., designations which may be input at a client device 101 and/or computing device 102).

Computing device 102 may also be configured to obtain electronic medical records associated with a plurality of patients and determine whether one or more patients may be eligible for a trial based on a patient-trial matching algorithm and electronic medical records. For example, computing device 102 may obtain electronic medical records associated with the patients of one or more clinics (e.g., a clinic associated with client device 101). Electronic medical records (EMRs) may include a variety of patient information, such as a patient name, a patient age, a patient gender, a medical identification number, a physician name, a care center name, a visit date, a visit result, a test, a test result, a biomarker indicator, a diagnosis, a prognosis, a medication, a dosage, a disease, a medical condition, and/or any other information relevant to patient health. Such information may be stored and/or received as a combination of structured and/or unstructured information. For example, structured information generally refers to information organized into a predetermined data structure, such as a combination of data fields. Unstructured information, on the other hand, generally refers to information that is not in a particular structure, and thus may not exist in a language immediately readable by a machine (e.g., handwritten text to which optical character recognition may be applied to help convert the text to machine-readable data). In some embodiments, client device 101 and/or computing device 102 may be configured to parse unstructured information to generate structured information for a predetermined data structure, which may be user-configurable. In further embodiments, client device 101 and/or computing device 102 may be configured to parse unstructured information to make predictions about the likelihood of certain events (e.g., the occurrence of genomic testing).

Additionally, client device 101 and/or computing device 102 may be configured to receive and/or process input information for a computerized model (e.g., a patient-trial matching model, neural network model based on neural network 300A). For example, client device 101 may include or may be connected to a scanning device, which may scan documents (e.g., documents containing unstructured data) associated with a patient. For example, a scanning device (e.g., a portable document scanner) may scan a handwritten note from a doctor and convert it to an image or other data entity (e.g., structured data). Computing device 102 may determine one or more patients among the patients of the clinic who may be eligible for a trial based on a patient-trial matching algorithm and electronic medical records (e.g., records that include structured and/or or unstructured data) and associated patient documents either included in the electronic medical records or otherwise associated with a patient.

By way of example, computing device 102 may create a namedtuple that has a combination of numbers and/or letters for each of the patients based on the electronic medical records (e.g., age, disease, biomarkers). Computing device 102 may evaluate the created namedtuples associated with the patients against the expression tree, which may return a number indicating the eligibility for each of the patients. For example, the expression-tree algorithm may output "0" for ineligible or "1" for eligible. Alternatively, the algorithm may output a probability value (e.g., a non-whole number) indicating the eligibility for each of the patients. Using the output of the expression-tree algorithm, patients may be matched to trials. For example, computing device 102 may determine the patients receiving an output of "1", or of a value within a predetermined distance of "1", and may transmit patient information associated with those patients to a client device 101 (e.g., to cause client device 101 to display information related to those patients, such as a biomarker).

Computing device 102 may further be configured to output one or more suggested eligible patients for the new trial. For example, computing device 102 may output one or more suggested patients to an output device (e.g., a display, printer). Alternatively or additionally, computing device 102 may transmit instructions for displaying information representing the one or more suggested patients to client device 101, which may present the information to the user.

In some embodiments, computing device 102 may be configured to provide one or more suggested trials for a patient. For example, the user may select a patient via the input device of client device 101 (or computing device 102), and computing device 102 may provide one or more trials for which the patient may be eligible based on one or more patient-trial matching algorithms and the electronic medical record associated with the patient.

In some embodiments, client device 101 and computing device 102 may be integrated into one device configured to perform the functions of client device 101 and computing device 102 disclosed herein. For example, a user may input information for creating a new trial via input device 153 of computing device 102, which may display one or more suggested patients for the new trial via an output device (e.g., output device 154, discussed below).

Database 103 may be configured to store information and data for one or more components of system 100. For example, database 103 may store electronic medical records associated with one or more patients. Database 103 may also store information relating to one or more trials. For example, database 103 may store trial eligibility criteria associated with each of the trials, such as a genomic testing criterion. In some embodiments, database 103 may also store patient-trial matching algorithms for determining one or more suggested eligible patients for a trial, and/or one or more suggested eligible trials for a patient. Client device 101 and/or computing device 102 may be configured to access and obtain the data stored on database 103 via network 104. In some embodiments, database 103 may be operated by a third party. For example, computing device 102 may request information relating to a particular trial from database 103, which may transmit the requested information to computing device 102. By way of example, computing device 102 may request the information of trial by transmitting a trial identifier (e.g., an NCT number) to database 103, which may transmit the requested information (e.g., trial eligibility criteria) to computing device 102.

Network 104 may be configured to facilitate communications among the components of system 100. Network 104 may include a local area network (LAN), a wide area network (WAN), portions of the Internet, an Intranet, a cellular network, a short-ranged network (e.g., a Bluetooth™ based network), or the like, or a combination thereof.

Figure 2:
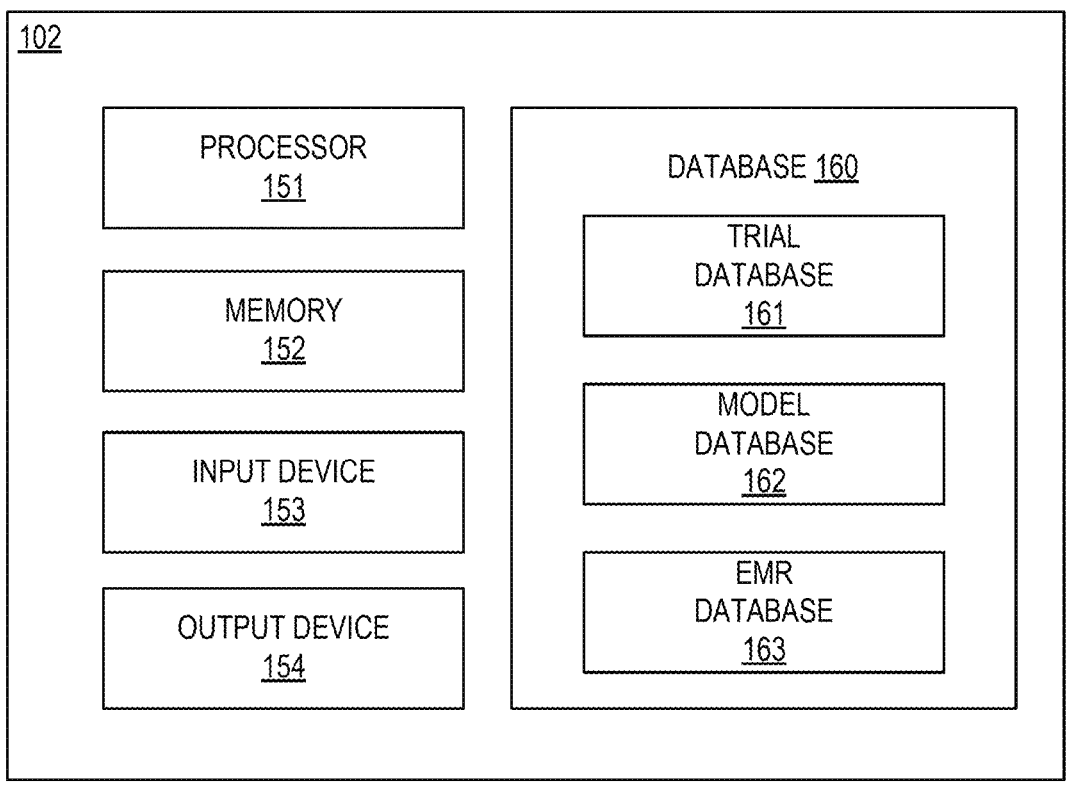
FIG. 2 is a block diagram illustrating an exemplary computing device for providing one or more suggested patients for a trial or one or more suggested trials for a patient, consistent with the present disclosure.

FIG. 2 is a block diagram illustrating an exemplary computing device 102. Computing device 102 may include at least one processor (e.g., processor 151), a memory 152, an input device 153, an output device 154, and a database 160.

Processor 151 may be configured to perform one or more functions described in this application. As mentioned, computing device 102 may include memory 152 that may store instructions for various components of computing device 102. For example, memory 152 may store instructions that, when executed by processor 151, may be configured to cause processor 151 to perform one or more functions described herein.

Input device 153 may be configured to receive input from the user of computing device 102, and one or more components of computing device 102 may perform one or more functions in response to the input received. In some embodiments, input device 153 may include a touchscreen, a keyboard, a microphone, a speaker, a haptic device, a camera, a button, a dial, a switch, a knob, a touch pad, a button, a microphone, a location sensor, an accelerometer, a camera, a fingerprint scanner, a retinal scanner, a biometric input device, an ultrasonic scanner, a transceiver, an input device, an output device, or other input device to perform methods of the disclosed embodiments. For example, input device 153 may include an interface displayed on a touchscreen (e.g., output device 154). Output device 154 may be configured to output information and/or data to the user. For example, output device 154 may include a display configured to display one or more suggested patients for a trial (e.g., a light-emitting diode (LED) display, a liquid crystal display (LCD) display, etc.). In some embodiments, output device 154 may include a touchscreen.

Database 160 may be configured to store various data and information for one or more components of computing device 102. For example, database 160 may include a trial database 161, a model database 162, and an electronic medical record (EMR) database 163. Trial database 161 may be configured to store information relating to one or more trials. For example, trial database 161 may store a trial portfolio for each of the trials, which may include trial eligibility criteria of a trial. Trial eligibility criteria of a trial may include a trial status, a trial disease, a trial line of therapy, an eligibility age, a trial biomarker criterion, a predicted genomic testing criterion, a verified genomic testing criterion, or the like, or a combination thereof. Of course, a criterion may include a presence of a particular attribute (e.g., having a particular genomic testing status), or may include an absence of a particular attribute (e.g., not having a particular genomic testing status). In some embodiments, a trial portfolio may also include trial name, trial description, or the like, or a combination thereof. Trial database 161 may further store an edit history including changes made to a trial. Computing device 102 may obtain information relating to the trials from trial database 161 and modify the information if needed. For example, computing device 102 may create a trial portfolio for a new trial and store the trial portfolio into trial database 161.

Model database 162 may store patient-trial matching models or algorithms. A patient-trial matching algorithm refers to an algorithm for determining one or more eligible patients for a trial and/or for determining one or more suggested eligible trials for a patient. A patient-trial matching algorithm may include a number of machine-configured and/or user-configured expressions, variables, data mappings, and/or other algorithm parameters, which may create connections between different information, such as patient data and user-selected trial parameters. Algorithm parameters may be updated based on subsequent datasets of patient information, to provide desirable outputs. Computing device 102 may obtain algorithms from model database 162. In some embodiments, computing device 102 may create an algorithm for a new trial and store the created algorithm into model database 162. A patient-trial matching model may be a computerized model, such as a machine learning model, a data model, a statistical model, a recurrent neural network (RNN) model, a long-short term memory (LSTM) model, and/or a neural network model (e.g., implementing neural network 300A), consistent with the disclosed embodiments. A patient-trial matching model may be trained or untrained, and may be supervised or unsupervised. EMR database 163 may store electronic medical records associated with patients. Processor 151 may receive one or more electronic medical records from EMR database 163.

Figure 3A:
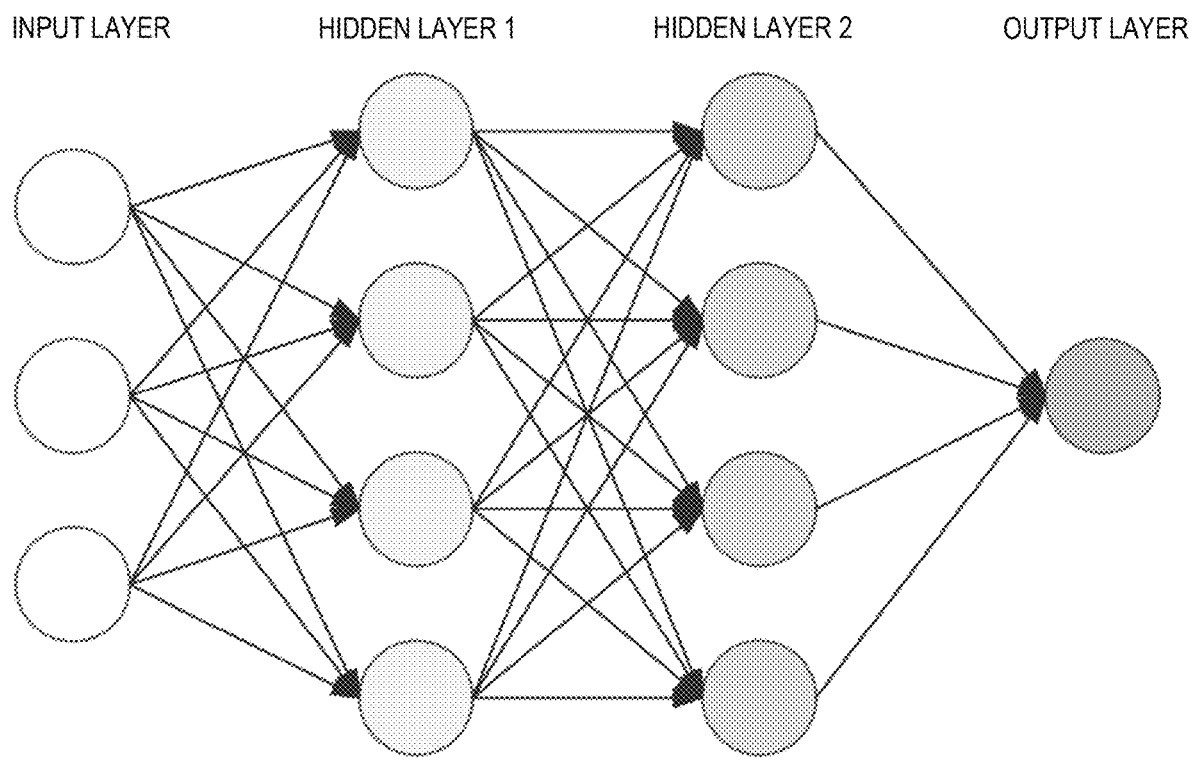
FIG. 3A is a diagram illustrating an exemplary neural network for providing patient information, consistent with the present disclosure.

FIG. 3A illustrates an exemplary neural network 300A. Neural network 300A may include an input layer, one or more hidden layers, and an output layer. Each of the layers may include one or more nodes. In some embodiments, the output layer may include one node. Alternatively, the output layer may include a plurality of nodes, and each of the nodes may output data. The input layer may be configured to receive input (e.g., an electronic medical record associated with a patient). In some embodiments, every node in one layer is connected to every other node in the next layer. A node may take the weighted sum of its inputs and pass the weighted sum through a non-linear activation function, the results of which may be output as the input of another node in the next layer. The data may flow from left to right, and the final output may be calculated at the output layer based on the calculation of all the nodes. Neural network 300A may output a probability indicating eligibility of the patient for the trial, which may be based on information from a received input. A neural network, such as neural network 300A, may be used to predict a genomic testing status of a patient. For example, some nodes of neural network 300A may be associated with information determined from patient information (e.g., structured and/or unstructured information), user inputs (e.g., user-defined parameters for the neural network), verified genomic testing statuses, previous neural network outputs, and/or any other data for informing configuration of neural network 300A.

In some embodiments, computing device 102 may determine a patient-trial match between a plurality of patients and a plurality of trials, based on the patient-trial matching algorithms associated with the trials and electronic medical records of the patients. For example, computing device 102 may determine one or more suggested eligible patients for each of the trials and/or one or more suggested eligible trials for each of the patients. Computing device 102 may also generate a data structure representing the relationship between the patients and trials and store the data structure in a database (e.g., database 103, database 160). Computing device 102 may further present the data representing the relationship between the patients and trials to the user. For example, computing device 102 may be configured to generate a patient-trial matching report. By way of example, computing device 102 may receive user input for defining filters for the data to appear on the report, including, for example, patient information (e.g., gender, age, location, patient schedule, diagnosis, biomarker, predicted genomic testing status, verified genomic testing status, or the like, or a combination thereof), treatment information (e.g., treatment, inclusionary and/or exclusion drug), and trial information (trial name, study drug, sponsor, study type, trial description, diagnosis, biomarker criteria, line of therapy, or the like, or a combination thereof). Computing device 102 may compile the patients and/or trials that match the filtered data into a report.

Figure 3B:
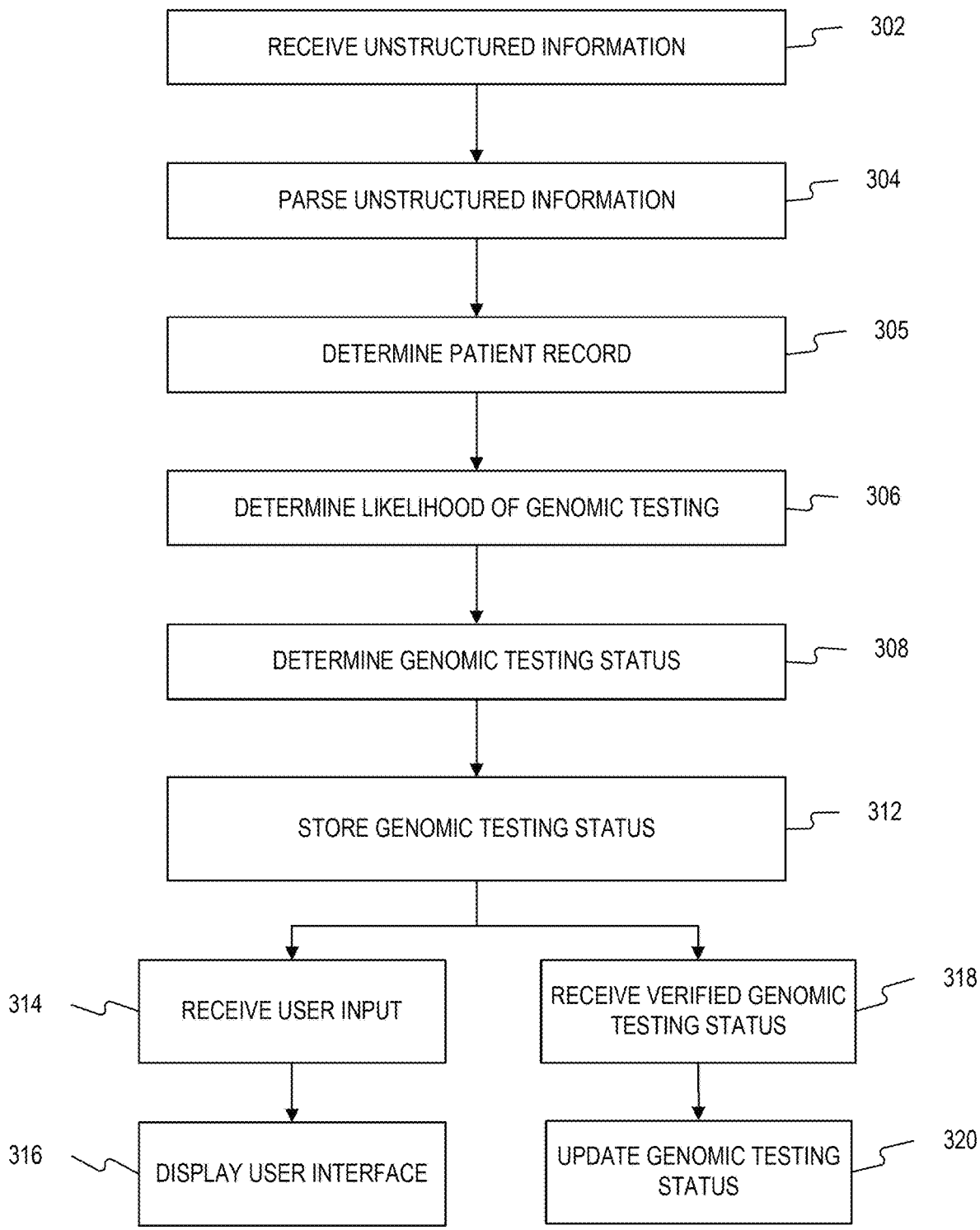
FIG. 3B is a flowchart illustrating an exemplary process for determining a genomic testing status.

FIG. 3B is a flowchart illustrating an exemplary process 300B for predicting the likelihood of an occurrence of a genomic testing for a patient and determining a patient's genomic testing status based on the predicted likelihood, consistent with the present disclosure. While process 300B is described in connection with client device 101, one skilled in the art would understand that one or more steps of process 300B may be performed by other components of the system (e.g., computing device 102 or processor 151). Alternatively or additionally, some steps of process 300 may be performed by multiple client devices 101, multiple computing devices 102, or any combination of devices. One of skill will understand that the steps illustrated in FIG. 3B are exemplary and steps may be added, merged, divided, duplicated, repeated, modified, performed sequentially, performed in parallel, and/or deleted in some embodiments.

At step 302, client device 101 may receive unstructured information associated with a patient (or multiple patients) from a source (or multiple sources). In some embodiments, a source may be remote from client device 101, or may be client device 101 itself. In some embodiments, unstructured information may be included in one or more patient records such as a scanned document, an unstructured field included or otherwise associated with an EMR (e.g., a handwritten or electronic note), and/or other representation of patient information. In some embodiments, unstructured information may include medical data associated with the patient (e.g., a genomic testing status, a test result, a patient age, a type of disease, a disease stage, etc.).

At step 304, client device 101 may parse unstructured information (e.g., unstructured information in a patient record). In some embodiments, parsing unstructured information may include identifying patterns or information contained in a record (e.g., identifying an occurrence of genomic testing for a patient, identifying a patient name, a physician name, a lab name, a test date, an admittance date, a line of therapy, a drug, etc.). In further embodiments, parsing unstructured information may include converting all or a portion of a record to a structured format. By way of example, a record may be an electronic record having structured and/or unstructured information (e.g., a Portable Document Format (PDF) record, an Extensible Markup Language (XML) file, etc.), an image, a chart, a drawing, or any other source of medical information. In some embodiments, an electronic record may be generated by a scanning device (e.g., a portable document scanner, a multi-functional printer, etc.), which may be connected to network 104. In some embodiments, the plurality of patient records may include at least one electronic record generated by scanning a physical document with a scanning device. For example, a scanning device may scan a physical document and generate an electronic record, which may include unstructured information from the physical document.

In some embodiments, parsing unstructured information may include identifying patterns and/or other information associated with genomic testing information and/or extracting genomic testing information, which may be used to categorize and/or prioritize patient records (e.g., step 305), predict a likelihood of an occurrence of genomic testing (e.g., step 306), and/or a genomic testing status (e.g., step 308). In some embodiments, identified genomic testing patterns or information and/or extracted genomic testing information may be associated with a patient identifier (e.g., linked to an electronic record of a patient identified in a document). In some embodiments, a trained model (e.g., implemented by a computing device 102) may parse unstructured information. A trained model may be, without limitation, any one of a computer software module, an algorithm, a machine learning model, a data model, a statistical model, a recurrent neural network (RNN) model, a long-short term memory (LSTM) model, or another neural network model (e.g., neural network 300A), consistent with the disclosed embodiments. A trained model may be implemented at computing device 102 or another computing device connected to network 104. In some embodiments, at least two trained models may be used. For example, one trained model to categorize and/or prioritize patient records (step 305) and a second trained model to predict an occurrence of genomic testing for a patient (step 306).

In further embodiments, genomic testing information may be identified from structured information (e.g., structured information that is part of a patient dataset). In some embodiments, when genomic testing information is included in structured information, the step of predicting the likelihood of genomic testing may be omitted. In some embodiments, structured information may be associated with unstructured information. For example, structured information and unstructured information may be associated with the same patient (e.g., part of a same EMR) and structured information may also be received at step 302).

In some embodiments (e.g., as part of step 305), client device 101 may categorize a plurality of patient records into record categories, which may be associated with different degrees of reliability. Client device 101 may also determine a priority order of the plurality of patient records (e.g., based on the record categories), which may be used in a subsequent step (e.g., step 306). By way of example, determining the priority order may include ordering the plurality of patient records based on dates associated with the plurality of patient records (e.g., placing records with a more recent date higher in the priority order). As yet another example, priority order may include ordering the plurality of patient records based on predefined record categories (e.g., a lab record category, a pathology record category, a genetic counseling record category, a healthcare provider notes category, a textual content category, etc.).

At step 305, client device 101 may determine a patient record from among a plurality of patient records. In some embodiments, a determined patient record may be considered a primary patient record, which may indicate that it has a relatively higher influence on a prediction, or is otherwise notable for a user. In some embodiments, client device 101 may determine a primary patient record using a first machine learning model. In some embodiments, at least a portion of information represented in a primary patient record may correlate (e.g., determined by a machine learning model) to genomic testing information. For example, a first machine learning model may be configured to associate record attributes, such as particular words, combinations of words, word frequencies, record formats, record sources (e.g., a lab), other record attribute, or combination thereof, with an occurrence of genomic testing. In some embodiments, a client device 101 may determine that a record (e.g., primary patient record) is from a particular record category and may determine that the record is a primary patient record (e.g., using a first machine-learning model) based on the determination that the primary patient record is from the particular record category.

In some embodiments, a client device 101 (e.g., using a processor) may determine the primary patient record based on a comparison of the correlation to a threshold. For example, a client device 101 may determine that the record has a correlation with a sufficient combination (e.g., according to model weights or other factors) of record attributes correlated with the occurrence of genomic testing. In some embodiments, client device 101 may receive the threshold from an entity associated with the client device (e.g., a client device configured to display a user interface). For example, a particular threshold may be associated with (e.g., set by) a particular research entity, clinic, etc. In some embodiments, a patient record (e.g., primary patient record) may be linked to a determination (e.g., a prediction of a likelihood of whether a patient has undergone genomic testing). In some embodiments, a primary patient record may be determined after a determination of a likelihood that a patient has had genomic testing (e.g., at step 306 or after step 308). In still yet further embodiments, step 305 may include identifying a plurality of patient records.

At step 306, client device 101 may determine a likelihood that a patient has had genomic testing (e.g., likelihood of an occurrence of genomic testing) to determine a patient testing status (e.g., "tested," "untested," "not enough information," and/or any information associated with a degree of testing for a patient). In some embodiments, client device 101 may determine the likelihood that a patient has had genomic testing using a second machine learning model and/or based on at least one of the patient records. For example, a second machine learning model may use structured and/or unstructured information parsed from at least one patient record to predict a likelihood of an occurrence of genomic testing for a patient (e.g., a likelihood that a patient has been tested for a genomic biomarker). A machine learning model may have been trained using combinations of patient records, genomic testing statuses, and user inputs. In some embodiments, client device 101 may determine the likelihood of a genomic testing occurrence of a patient according to a priority order of the plurality of patient records (e.g., determined at step 305). A likelihood that a patient has had genomic testing may be represented as a combination of a percentage and a genomic testing status (e.g., 80% chance of "tested" status, 10% chance of "untested" status, 10% chance of "not enough information" status, etc.). In some embodiments, a likelihood that a patient has had genomic testing may be represented as multiple such combinations. In other embodiments, a likelihood that a patient has had genomic testing may be represented as a number (e.g., a percentage). In some embodiments, a client device 101 may determine a likelihood that a patient has had genomic testing periodically. For example, client device 101 may determine a likelihood of a genomic testing of a patient periodically using at least one of: a time period measured in hours, a time period measured in days, or a time period determined based on a frequency of receiving new patient records. In some embodiments, client device 101 may update a likelihood of a genomic testing of a patient after receiving additional patient records. For example, after receiving a new record of a particular type (e.g., a lab report), a threshold number of records (e.g., two records related to a patient) and/or after a threshold number of patient visits to a clinic (e.g., determined from a medical record, user input, etc.), client device 101 may be triggered to update a patient's likelihood of genomic testing.

At step 308, client device 101 may determine a genomic testing status of a patient based on a determined likelihood of an occurrence of genomic testing for a patient (e.g., determined at step 306). A genomic testing status may include "likely," "unlikely," "possibly," "not enough information," and/or any other information indicating a likelihood that a patient has had genomic testing. For example, client device 101 may determine a particular genomic testing status if that status had an associated likelihood reaching a threshold (e.g., 85% chance of having one status, 10% chance of having another status). In some embodiments, a genomic testing status may cause a change to a displayed user interface (e.g., such that a user interface may be dynamic, even after being displayed). For example, additional patient information may be displayed within a feasibility analysis based on a genomic testing status.

At step 312, client device 101 may store a genomic testing status (e.g., determined at step 308). For example, client device 101 may store a genomic testing status of a patient at database 103, memory 152, database 160, and/or any other storage medium. In some embodiments, client device 101 may associate an indicator of the genomic testing status of a patient with a patient identifier of the patient, and may store the association among a plurality of other associations (e.g., associations for other patients) in a database (e.g., database 103). For example, client device 101 may associate a genomic testing status with a particular patient, such as through a data binding, and may store the data binding together with the genomic testing status. In some embodiments, such as after performing step 312, process 300B may proceed to step 314, which relates to a user input. Additionally or alternatively, process 300B may proceed to step 318, which relates to a verified genomic testing status. As all steps in process 300B are optional, re-arrangeable, repeatable, and capable of simultaneous performance, in some embodiments, for example, process 300B may include steps 314 and 316, but not steps 318 or 320. Of course, the opposite is also true, as well as the fact that in some embodiments, process 300B may include all of steps 314-320.

In some embodiments, process 300B may include step 314, at which client device 101 may receive a user input, which may be a request to display particular information. For example, client device 101 may receive a user input (e.g., an input to a user interface displayed at output device 154) to display patient information, such as a genomic testing status and/or at least one document used to determine the likelihood of genomic testing for a patient. In some embodiments, client device 101 may receive a user input at one of the user interfaces described with respect to FIGS. 4A-6C. By way of example, computing device 102 may receive a search request (e.g., for feasibility analysis) from a remote device (e.g., a client device 101). The search request may include at least one parameter associated with a genomic testing status of a patient (e.g., a parameter requesting patient information associated with genomic testing statuses of "verified tested," "tested," "likely tested," etc.). In some embodiments, computing device 102 may access testing criteria for a patient, which may be done in response to a user input. Such testing criteria may include a testing practice, a timeline, a regulatory criterion, etc., which may be used to generate a notification or other information (e.g., at step 316).

At step 316, client device 101 may display a user interface, which client device 101 may determine based on user input received at step 314. Client device 101 may be configured to display a user interface at an output device 154 using data stored at memory 152. In some embodiments, client device 101 may display a user interface described with respect to any of FIGS. 4A-6C. In some embodiments, client device 101 may retrieve an indicator of a genomic testing status of a patient and/or a patient identifier in response to a search request received from a remote device. In some embodiments, client device 101 may display a user interface comprising an indicator of a genomic testing status of a patient and a link to a primary patient record, which may be correlated with the genomic testing status of the indicator. In some embodiments, computing device 102 may transmit a notification to a remote device, which may be based on at least one testing criterion (e.g., received at step 314) and/or the genomic testing status of the patient (e.g., "not tested"). By way of example, computing device 102 may determine that a patient genomic testing status does not satisfy at least one testing criterion (e.g., timeline) and may transmit a notification to, for example, a client device 101, to alert a physician or other user.

In some embodiments, the user interface may include an indicator of a biomarker associated with the patient (e.g., a biomarker for which the patient has been tested, a biomarker test result, etc.). In some embodiments, client device 101 determine the biomarker based on a user input received via the user interface (e.g., at an interactable element 406B, 406E, etc.). In some embodiments, client device 101 may determine the biomarker using a third machine learning model. For example, a third machine learning model may interpret information from a patient record to predict a biomarker associated with a patient. To further this example, in some embodiments, the third machine learning model may interpret records associated with genomic testing to determine biomarker information, which the third machine learning model may use to predict a biomarker associated with a patient. In some embodiments, a notification may be transmitted to an application at a remote device that is configured to display a user interface (e.g., a user interface discussed with respect to FIGS. 4A-6C) and a primary patient record.

In some embodiments, process 300B may include step 318, at which client device 101 may receive an input comprising a verified genomic testing status of the patient. For example, a client device 101 may receive an input that a patient has a verified status of "tested" or "not tested," which may be indicated by a user input (e.g., a selection of a selector 404D), or otherwise indicated in a structured field. Such an input may prevent a machine learning model (e.g., a machine learning model for predicting a likelihood of a genomic testing status) from running, which may reduce strain on computing resources. For example, in some embodiments, a machine learning model may be configured to only predict genomic testing status likelihoods for patients having a predicted likelihood of a genomic status, no predicted likelihood of a genomic status, or a verified status of "not tested." Step 318, as with any step in process 300B or any other process herein, may occur concurrently with other steps. For example, a client device 101 (or other device) may receive a verified genomic testing status while also receiving a user input.

At step 320, client device 101 may update a genomic testing status of a patient, which may be based on a verified genomic testing status. In some embodiments, client device may transmit the verified genomic testing status to a remote device (e.g., database 103). In some embodiments, client device 101 may change at least one parameter of the first machine learning model based on the verified genomic testing status of the patient. For example, the verified genomic testing status of the patient and at least one patient record associated with the patient may be used to train a machine learning model to predict a likelihood of a genomic testing status. As yet another example, client device 101 may add, remove, and/or modify a node and/or layer of a neural network In some embodiments, a verified genomic testing status may cause a change to a displayed user interface (e.g., such that a user interface may be dynamic, even after being displayed). For example, additional patient information may be displayed within a feasibility analysis based on a verified genomic testing status.

FIGS. 4A-4F, 5, and 6A-6C illustrate exemplary user interfaces for managing patient genomic testing information, consistent with the present disclosure. Any of the exemplary user interfaces described herein may be displayed via output device 154 of computing device 102 (e.g., a display or touchscreen), and the user may enter information via input device 153. Alternatively or additionally, computing device 102 may transmit instructions to client device 101 for displaying a user interface via an output device of client device 101 (e.g., a display or touchscreen) and for receiving user input via an input device of client device 101. As described below, user interfaces may include a region, indicator, link, and/or other graphical element (interactable or non-interactable). Any or all of the graphical elements discussed below, with respect to any of the user interfaces, may be re-arranged, duplicated, added, and/or removed. Using user interface 400A in FIG. 4A as an example, region 404 may be placed above region 406, which in turn may appear above region 402. As another example, in FIG. 4A, additional displayed elements may be ordered differently in the graphical element (e.g., the elements may be ordered in the graphical element in the following order: region 404, link 404C, region 406, and region 402).

Exemplary FIG. 4A illustrates a user interface 400A which may display graphical (e.g., interactable) elements, which may show information about a patient, including a predicted likelihood of an occurrence of genomic testing. User interface 400A may include a region 402, which may include information about at least one biomarker associated with a patient (e.g., a biomarker type, a biomarker result, a lab identification, etc.).

User interface 400A may also include a region 404, which may include information about a genomic testing status of a patient, which may include an inferred genomic testing status (e.g., based on a predicted likelihood). For example, region 404 may include an indicator 404A, which may indicate an inferred likelihood of a genomic testing status (e.g., "likely"). Region 404 may also include an indicator 404B, which may display a date when the likelihood of a genomic testing occurrence was determined, updated, or otherwise influenced (e.g., by a received record, user input, etc.). Region 404 may also include a link 404C, which may link to a record associated with the likelihood. For example, selection of link 404C may cause a record to display within a display that is displaying user interface 400A. Such a record may display in a separate window and/or application, such as is shown with respect to exemplary FIG. 5. Region 404 may also include at least one selector 404D, which may be interactable by a user to confirm/verify a genomic testing status of a patient (e.g., "tested," "not tested"). In some embodiments, selection of a selector 404D may cause another user interface to be displayed (e.g., user interface 400B)

User interface 400A may also include a region 406, which may include graphical elements for managing information related to a biomarker. For example, region 406 may include biomarker information for a particular patient and/or interactable elements, such as link 406A, which, after being selected, may display additional elements, such as interactable elements. For example, link 406A may be selected to allow for biomarker information to be added to a patient record and/or displayed within a user interface.

User interface 400A may also include a region 408, which may include graphical elements related to a drug order history of a patient. Information in region 408 may be sourced from a remote device, such as a user device associated with a physician, a pharmacy, etc. Information in region 408 may also be dynamic, thus allowing for real-time updates to be displayed within user interface 400A or another user interface.

Exemplary FIG. 4B illustrates a user interface 400B which may display graphical (e.g., interactable) elements, which may show information about a patient, including a prediction of whether a patient has had genomic testing. User interface 400B may include regions in elements discussed with respect to other figures (e.g., region 402, 404, 406, and/or 408). User interface 400B may also include a link 404F and/or indicators 404E, which may be displayed within region 404. Link 404F may be selectable and may allow a user to change a genomic testing status of a patient (e.g., displayed within a region 404). Indicators 404E may indicate a verified genomic testing status and/or information associated with an update to a genomic testing status (e.g., a user identifier associated with a user who updated the status, a time an update was made, etc.).

Exemplary FIG. 4C illustrates a user interface 400C which may display graphical (e.g., interactable) elements, which may show information about a patient, including a predicted likelihood that genomic testing has occurred for a patient. User interface 400C may include regions discussed with respect to other figures (e.g., region 402, 404, 406, and/or 408). User interface 400C may also include interactable elements 406B, which may be displayed within region 406. Interactable elements 406B may be configured to allow a user to add information to a patient record, which may be related to a biomarker. For example, interactable elements 406B may include a drop-down menu, slider bar, calendar widget, text box, and/or any other graphical user interface element that may allow a user to enter information related to a biomarker. Region 406 may also include link 406C, which may be usable to finalize entry of data into interactable element 406B. For example, after being selected, link 406C may cause a device to verify information in interactable elements 406B as valid (e.g., determining that a vendor indicator input by a user is associated with a vendor that offers a test type also entered by the user, determining that a result date is not a future date, etc.). After being selected, link 406C may cause a device to display another user interface and/or update a patient record (e.g., with updated biomarker information).

Exemplary FIG. 4D illustrates a user interface 400D which may display graphical (e.g., interactable) elements, which may show information about a patient, including a predicted likelihood that genomic testing has occurred for a patient. User interface 400D may include regions in elements discussed with respect to other figures (e.g., region 402, 404, 406, and/or 408). User interface 400D may also include indicators 406D and/or link 406A. Indicators 406D may display information associated with a biomarker captured for a patient (e.g., information which may have at least partially been entered using interactable elements 406B, such as a type of biomarker, a lab entity, a biomarker result, a result date, etc.). Indicators 406D may include interactable elements, which may allow a user to edit associated information. In some embodiments, after being selected, link 406A may cause a user interface 400E, shown in exemplary FIG. 4E, to be displayed. User interface 400E may include interactable elements 406E, which may be displayed within region 406 and may be similar to interactable elements 406B.

Exemplary FIG. 4F illustrates a user interface 400F which may display graphical (e.g., interactable) elements (e.g., including region 402, 404, 406, and/or 408), which may show information related to multiple biomarkers. For example, user interface 400F may include an indicator 406D, which may include information for a first biomarker, and indicator 406F, which may include information for a second biomarker.

Figure 5:
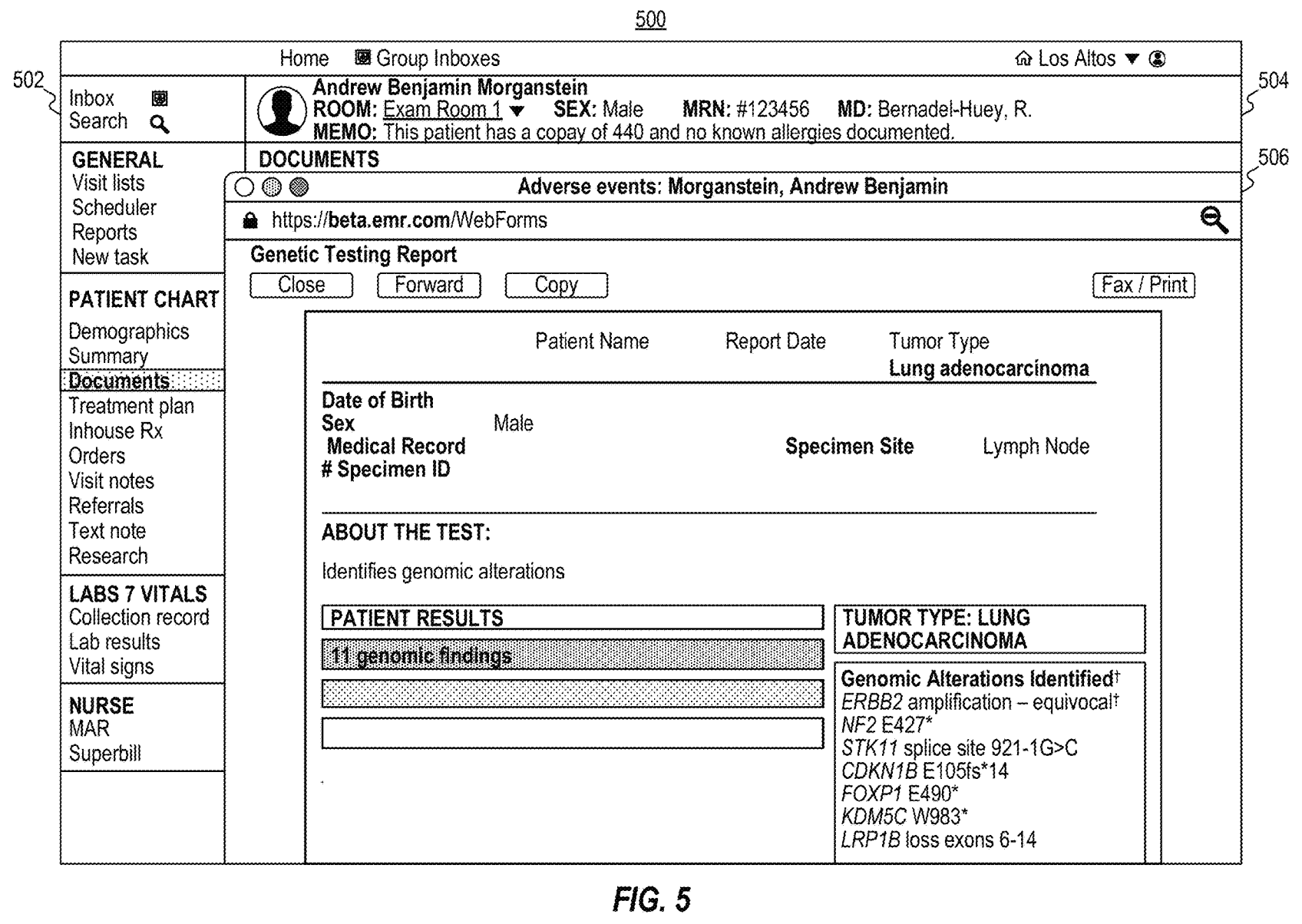

Exemplary FIG. 5 illustrates a user interface 500 for surfacing patient records. User interface 500 may include a sidebar 502, which may include any number of interactable elements for determining a record that may be relevant to a patient (e.g., which may have influenced a prediction of a genomic testing likelihood or status, such as a search bar, text box, button, slide bar, filter, link, etc.). User interface 500 may also include a patient information panel 504, which may include information related to a patient associated with a surfaced patient record (e.g., a patient name, a patient sex, a patient identification number, a patient physician identifier, a patient memo, a patient age, and/or any other patient information). In some embodiments, user interface 500 may include a record display window 506, which may include a record (e.g., a scanned patient document, structured patient information, unstructured patient information, a lab test document, etc.). A record may be sourced from an external source (e.g., a client device 101, database 103, a scanning device, and/or any device associated with a medical service provider).

Exemplary FIG. 6A illustrates a user interface 600A, which may be associated with performing a feasibility analysis. A feasibility analysis may be performed by a computing device 102, for example, to determine a group of patients, which may be based on criteria determined by a user. By enabling determinations of different groups of patients based on different parameters, a device performing a feasibility analysis may be able to provide insight into patient information, which may, for example, allow a user to determine if an adequate group of patients exists, based on patient information, for a particular purpose. For example, user interface 600A may include a feasibility analysis window 602, which may include information for determining patients for a trial. For example, analysis window 602 may include a first criteria region 604, which may include interactable elements that allow a user to input first criteria for a feasibility analysis. First criteria may relate to patient demographics and/or visits, and may include a gender criterion, a location criterion, an age criterion, a patient status criterion (e.g., deceased, living, new patient, old patient), a visit data criterion, etc. Analysis window 602 may also include a second criteria region 606, which may include interactable elements that allow a user to input second criteria for a feasibility analysis. Second criteria may include diagnostic criteria, such as a disease criterion, a testing status (e.g., genomic testing status) criterion, a biomarker criterion, a metastatic status criterion, etc. Analysis window 602 may also include a third criteria region 608, which may include interactable elements that allow a user to input third criteria for a feasibility analysis. Third criteria may include treatment-related criteria, such as a drug type criterion, a medication order data criterion, a drug dosage criterion, etc. Feasibility analysis window may also include a button 610 or other interactable element, which may instruct a device to perform a feasibility analysis using information within user interface 600A.

Exemplary FIG. 6B illustrates a user interface 600B, which may be similar to user interface 600A. For example, user interface 600B may include analysis window 602, which may further include a results region 612, which may include patient information determined by a feasibility analysis. For example, results region 612 may include information associated with patients satisfying a set of criteria. In some embodiments, patient information may be displayed within a table 614 or other graphical structure.

For example, as shown in exemplary FIG. 6C, a user interface 600C may be displayed (e.g., in response to a selection of button 610), which may display information associated with multiple patients. By way of example, patient information may be displayed within table 614, which different rows, such as exemplary rows 614a, 614b, and 614c, being associated with difference patients. A row (or other graphical element displaying patient information) may be removed, added, and/or altered in response to a user input (e.g., a checkbox selection, button selection, etc.).

Figure 7:
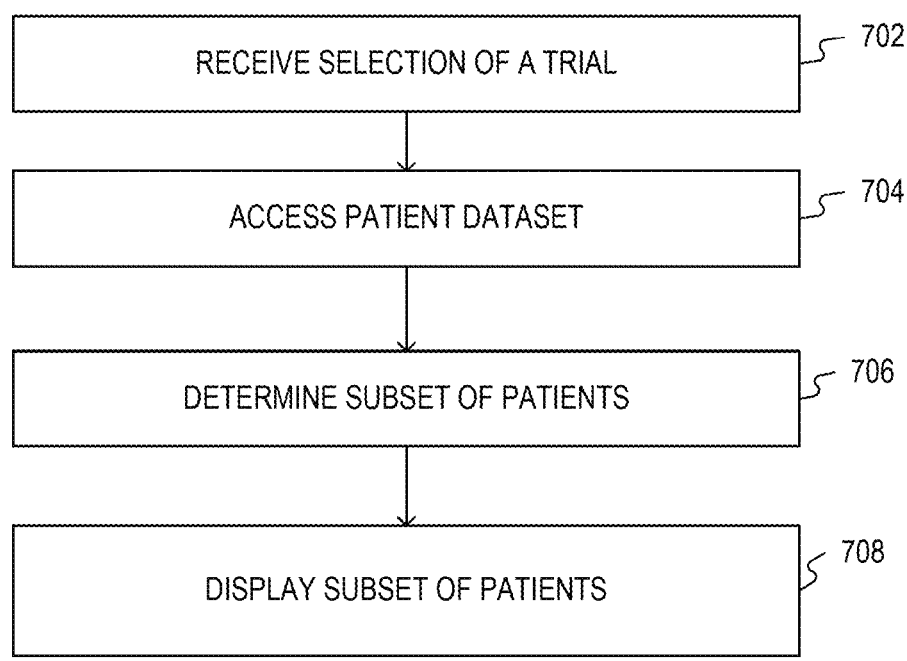
FIG. 7 is a flowchart illustrating an exemplary process for providing one or more suggested patients for a trial, consistent with the present disclosure.

FIG. 7 is a flowchart illustrating an exemplary process 700 for suggesting one or more patients for a trial, consistent with the present disclosure. While process 700 is described in connection with client device 101, one skilled in the art would understand that one or more steps of process 700 may be performed by other components of the system (e.g., computing device 102 or processor 151).

At step 702, client device 101 may receive a selection of a trial. For example, client device 101 may receive a user input via a user interface of client device 101 for selecting a trial. By way of example, the user may select a trial from a list of trials. In some embodiments, a user may search for a trial within a search interface (e.g., using a trial name, unique trial identifier, etc.).

At step 704, client device 101 may access a patient dataset. In some embodiments, client device 101 may access a patient dataset in response to a selection of the trial (e.g., at step 702). For example, an accessed patient dataset may be associated with a selected trial and/or trial criteria. Accessing a patient dataset may include retrieving a patient dataset from a database (e.g., database 103). In some embodiments, a patient dataset may be stored among a plurality of patient datasets at a database. By way of further example, client device 101 may send a request to retrieve a patient dataset from database 103 to computing device 102. In some embodiments, a request to retrieve a patient dataset may be formatted to include a unique patient information identifier or other information enabling computing device 102 to distinguish the requested patient dataset from among those stored at database 103.

At step 706, client device 101 may determine a subset of patients. In some embodiments, client device 101 may determine a subset of patients meeting criteria for a trial (e.g., a trial selected at step 702). For example, client device 101 may compare trial criteria and/or user-selected parameters to one or more patient profiles associated with different patients, to determine which patients may be suitable for a trial. Based on such a comparison, client device 101 may determine a subset of patient profiles, representing a subset of patients, within a set of patient profiles.

For example, determining a subset of patients may be based on at least a portion of a patient dataset, trial dataset, a likelihood of genomic testing, a genomic testing status, and/or a trial criterion. For example, a subset of patients may be determined based on a predicted or verified genomic testing status trial criterion (e.g., of a trial). In some embodiments, computing device 102 may use a patient dataset and/or genomic testing likelihood and/or genomic testing status to determine, from among a set of patients (e.g., represented by patient profiles stored at a database 103), patients for a subset. In some embodiments, a set of patients may be associated with a genomic testing status criterion (e.g., at least one genomic testing status criterion may be associated with a trial), which may be used in determining a subset of patients. For example, client device 101 may compare a genomic testing status (e.g., a predicted genomic testing status) with a genomic testing status criterion of a trial (e.g., "tested," "verified tested," etc.). In some embodiments, client device 101 may determine that the predicted genomic testing status of a patient satisfies the genomic testing status criterion of a trial (e.g., based on the comparison, client device 101 may determine that the predicted genomic testing status matches the genomic testing status trial criterion), and may then include that patient in the subset of patients, based on this determination. In some embodiments, client device 101 may determine that the predicted genomic testing status of a patient does not satisfy the genomic testing status criterion of a trial (e.g., based on the comparison, client device 101 determines that the genomic testing status does not match the genomic testing status trial criterion), and may then exclude that patient from the subset of patients, based on this determination.

At step 708, client device 101 may cause a display (e.g., at a display of client device 101) of a subset of patients for a trial (e.g., a subset determined at step 706). In some embodiments, computing device 102 may cause the display of a subset of patients for a trial at a client device 101. In some embodiments, causing display of a subset of patients may include displaying criteria of a trial and/or indicators of a patient qualification status for the criteria. As described with respect to other figures, displaying a subset of patients may include displaying at least one indicator, interactable element, etc., which may change dynamically based on updates to a patient dataset, a genomic testing status, at least one trial criterion, and the like.

Figure 8:
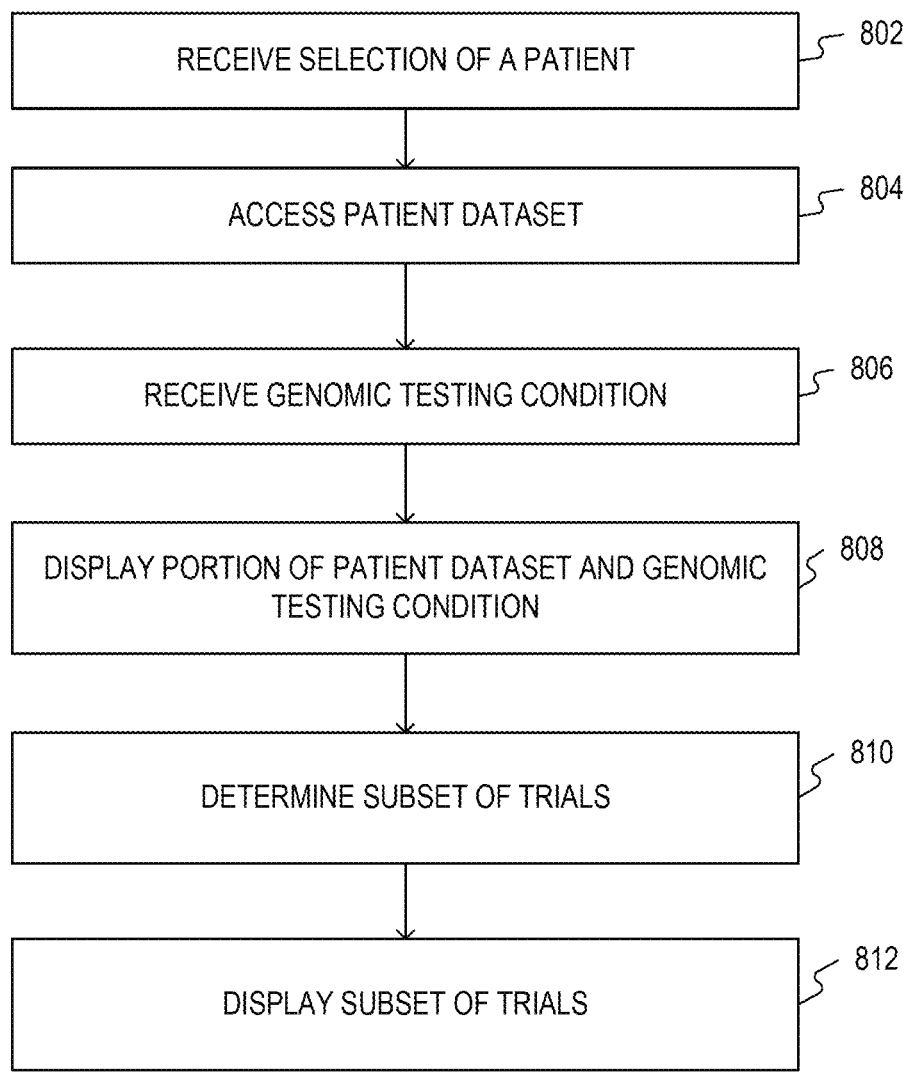
FIG. 8 is a flowchart illustrating an exemplary process for providing one or more suggested trials, consistent with the present disclosure.

FIG. 8 is a flowchart illustrating an exemplary process 800 for suggesting one or more patients for a trial, consistent with the present disclosure. While process 800 is described in connection with client device 101, one skilled in the art would understand that one or more steps of process 800 may be performed by other components of the system (e.g., computing device 102 or processor 151).

At step 802, client device 101 may receive a selection of a patient. For example, client device 101 may receive a user input via a user interface of client device 101 for selecting a patient. By way of example, the user may select a patient from a list of patients (e.g., within user interface 600C). In some embodiments, a user may search for a patient within a search interface (e.g., using a patient name, patient date of birth, unique patient identifier, etc.), such as user interface 600A prior to selecting a patient.

At step 804, client device 101 may access a patient dataset. In some embodiments, client device 101 may access a patient dataset in response to a selection a patient dataset in response to a selection of the patient (e.g., at step 802). For example, an accessed patient dataset may be associated with a selected patient (e.g., a genomic testing status and a patient identifier). Accessing a patient dataset may include retrieving a patient dataset from a database (e.g., database 103). In some embodiments, a patient dataset may be stored among a plurality of patient datasets at a database. By way of further example, client device 101 may send a request to retrieve a patient dataset from database 103 to computing device 102. In some embodiments, a request to retrieve a patient dataset may be formatted to include a unique patient identifier or other information enabling computing device 102 to distinguish the requested patient dataset from among those stored at database 103.

At step 806, client device 101 may receive a genomic testing status. In some embodiments, a received genomic testing status may be a verified genomic testing status or a genomic testing status based on a determined likelihood of genomic testing (e.g., as discussed in FIG. 3B). In some embodiments, a genomic testing status based on a prediction may be classified as "unknown" or "not enough information," such as in situations where a machine learning model determines it does not have sufficient input information to make a prediction. In some embodiments, a genomic testing status may be associated with a patient (e.g., a patient selected at step 802). A likelihood of genomic testing may have been predicted by a trained model configured to receive a patient record, which may include unstructured information. For example, computing device 102 may have received a patient record (e.g., from a client device 101, which may or may not be the same device performing a step of process 800), and may have applied a trained model to the record to extract information from the record and/or convert the record into a format having structured information. In some embodiments, a genomic testing status based on a prediction may include a degree of likelihood determined by the machine-learning model.

At step 808, client device 101 or computing device 102 may cause display of at least a portion of the patient dataset and a genomic testing status (e.g., a genomic testing status based on a prediction). For example, displayed portions may be displayed within a user interface (e.g., user interface 600C), consistent with disclosed embodiments. In some embodiments, the displayed portions may include a subset or entirety of the patient dataset accessed at step 802 and/or the genomic testing status received at step 806.

At step 810, client device 101 may determine a subset of trials for a patient. In some embodiments, determining a subset of trials for a patient may be based on at least a portion of the patient dataset or a likelihood of genomic testing and/or a genomic testing status (which may or may not be a same portion as of that in step 808). For example, a subset of trials may be determined based on a predicted likelihood of an occurrence of genomic testing or verified genomic testing status. By way of example, a first subset of trials may be determined based on a first genomic testing status (e.g., based on a predicted likelihood of an occurrence of genomic testing at a first time, and a second subset of trials may be determined based on a second genomic testing status (e.g., a verified genomic testing status) at a second time. In some embodiments, a subset of trials for a patient may be determined from a plurality of trials. By way of example, computing device 102 may use a patient dataset and/or genomic testing status to determine, from among a set of trials (e.g., stored at a database 103), trials for a subset. In some embodiments, a set of trials may be associated with a genomic testing status criterion (e.g., at least one genomic testing status criterion may be associated with each trial of the set), which may be used in determining a subset of trials. For example, client device 101 may compare a genomic testing status (e.g., a predicted genomic testing likelihood and/or status) with a genomic testing status criterion of a trial (e.g., "tested," "verified tested," etc.). In some embodiments, client device 101 may determine that the predicted genomic testing status satisfies the genomic testing status criterion of a trial (e.g., based on the comparison, client device 101 may determine that the predicted genomic testing status matches the genomic testing status criterion), and may then include that trial in the subset of trials, based on this determination. In some embodiments, client device 101 may determine that the predicted genomic testing status does not satisfy the genomic testing status criterion of a trial (e.g., based on the comparison, client device 101 determines that the genomic testing status does not match the genomic testing status trial criterion), and may then exclude that trial from the subset of trials, based on this determination.

At step 812, client device 101 may cause a display (e.g., at a display of client device 101) of a subset of trials for a patient (e.g., a subset determined at step 810). In some embodiments, computing device 102 may cause the display of a subset of trials for a patient at a client device 101. In some embodiments, causing display of a subset of trials may include displaying criteria of the subset of trials and/or indicators of a patient qualification status for the criteria. As described with respect to other figures, displaying a subset of trials may include displaying at least one indicator, interactable element, etc., which may change dynamically based on updates to a patient dataset, a genomic testing status, at least one trial criterion, and the like.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering, repeating, inserting, and/or deleting steps. It is intended, therefore, that the specification and examples be considered as illustrative only, with a true scope and spirit being indicated by the following claims and their full scope of equivalents.

What is claimed is:

1. A system for determining a genomic testing status of a patient, the system comprising:
    at least one processor programmed to:

receive, from a source, unstructured information from a plurality of patient records associated with a patient;

determine, using a first machine learning model, a primary patient record from among the plurality of patient records, wherein at least a portion of information represented in the primary patient record correlates to genomic testing;

determine, using a second machine learning model and based on unstructured information from one at least one of the patient records, a likelihood of an occurrence of genomic testing for the patient;

determine a genomic testing status of the patient based on the determined likelihood of the occurrence of genomic testing; and display on a computing device a user interface comprising an indicator of the genomic testing status of the patient and a link to the primary patient record.

2. The system of claim 1, wherein the at least one processor is further programmed to determine the primary patient record based on a comparison of a degree of correlation between the primary patient record and the genomic testing to a threshold.

3. The system of claim 2, wherein the at least one processor is further programmed to receive the threshold from an entity associated with a client device configured to display the user interface.

4. The system of claim 1, wherein the at east one processor is further programmed to:

categorize the plurality of patient records into record categories;

determine a priority order of the plurality of patient records based on the record categories; and determine the likelihood of the occurrence of genomic testing of the patient according to the priority order of the plurality of patient records.

5. The system of claim 4, wherein determining the priority order includes ordering the plurality of patient records based on dates associated with the plurality of patient records.

6. The system of claim 4, wherein the at least one processor is further programmed to:

determine that the primary patient record is from a particular record category; and determine the primary patient record, using the first machine learning model, based on the determination that the primary patient record is from a particular record category.

7. The system of claim 1, wherein the user interface further includes an indicator of a biomarker associated with the patient.

8. The system of claim 7, wherein the at least one processor is further programmed to determine the biomarker based on a user input received via the user interface.

9. The system of claim 7, wherein the at least one processor is further programmed to determine the biomarker using a third machine learning model.

10. The system of claim 1, wherein the at least one processor is further programmed to:

associate the indicator of the genomic testing status of the patient with a patient identifier of the patient;

store the association among a plurality of other associations in a database; and retrieve, in response to a search request received from a remote device, the indicator of the genomic testing status of the patient and the patient identifier, wherein the search request comprises a parameter associated with the genomic testing status of the patient.

11. The system of claim 1, wherein the at least one processor is further programmed to:

access testing criteria for the patient; and based on the testing criteria and the genomic testing status of the patient, transmit a notification to a remote device.

12. The system of claim 11, wherein the notification is transmitted to an application at the remote device configured to display the user interface and the primary patient record.

13. The system of claim 1, wherein the at least one processor is further programmed to determine the likelihood of the occurrence of genomic testing of the patient periodically.

14. The system of claim 13, wherein the occurrence of genomic testing of the patient is determined periodically using at least one of a time period measured in hours, a time period measured in days, or a time period determined based on a frequency of receiving new patient records.

15. The system of claim 13, wherein the at least one processor is further programmed to update the likelihood of the occurrence of genomic testing of the patient after receiving additional patient records.

16. The system of claim 1, wherein the at least one processor is further programmed to receive an input comprising a verified genomic testing status of the patient.

17. The system of claim 16, wherein the at least one processor is further programmed to transmit the verified genomic testing status to a remote device.

18. The system of claim 16, wherein the at least one processor is further programmed to change at least one parameter of the first machine learning model based on the verified genomic testing status of the patient.

19. The system of claim 1, wherein the plurality of patient records include at least one electronic record generated by scanning a physical document with a scanning device.

20. A method for determining a genomic testing status of a patient, comprising:

receiving, from a source, a plurality of patient records associated with a patient;

determining, using a first machine learning model, a primary patient record from among the plurality of patient records, wherein at least a portion of information represented in the primary patient record correlates to genomic testing;

determining, using a second machine learning model and based on at least one of the patient records, a likelihood of an occurrence of genomic testing for the patient;

determining a genomic testing status of the patient based on the determined likelihood of the occurrence of genomic testing; and displaying on a computing device a user interface comprising an indicator of the genomic testing status of the patient and a link to the primary patient record.

21. A non-transitory computer-readable medium comprising instructions that when executed by one or more processors, cause the one or more processors to:

receive, from a source, a plurality of patient records associated with a patient;

determine, using a first machine learning model, a primary patient record from among the plurality of patient records, wherein at least a portion of information represented in the primary patient record correlates to genomic testing;

determine, using a second machine learning model and based on at least one of the patient records, a likelihood of an occurrence of genomic testing for the patient;

determine a genomic testing status of the patient based on the determined likelihood of the occurrence of genomic testing; and display on a computing device a user interface comprising an indicator of genomic testing status of the patient and a link to the primary patient record.

* * * * *

UNITED STATES PATENT AND TRADEMARK OFFICE
CERTIFICATE OF CORRECTION

PATENT NO. : 11,004,541 B1
APPLICATION NO. : 17/076502
DATED : May 11, 2021
INVENTOR(S) : Addison Shelley et al.

Page 1 of 1

It is certified that error appears in the above-identified patent and that said Letters Patent is hereby corrected as shown below:

In the Claims

Claim 1, Column 21, Lines 10-11, "one at least one" should read as --at least one--.

Claim 4, Column 21, Line 28, "at east one" should read as --at least one--.

Signed and Sealed this
Sixteenth Day of January, 2024

Katherine Kelly Vidal
*Director of the United States Patent and Trademark Office*